United States Patent [19]
Ismail

[11] Patent Number: 5,948,769
[45] Date of Patent: Sep. 7, 1999

[54] AGENT FOR TREATING HEART DISEASES

[76] Inventor: Roshdy Ismail, Seibengebirgs-Apotheke Siebengebirgsallee 2, D-5000 Koln 41, Germany

[21] Appl. No.: 08/488,024

[22] Filed: Jun. 7, 1995

Related U.S. Application Data

[63] Continuation of application No. 08/137,940, Oct. 19, 1993, which is a continuation of application No. 07/913,885, Jul. 17, 1992, abandoned, which is a continuation of application No. 07/639,418, Jan. 10, 1991, Pat. No. 5,153,001, which is a continuation of application No. 07/290,848, Nov. 29, 1988, abandoned, which is a continuation of application No. 06/870,029, Jun. 3, 1986, abandoned, which is a continuation of application No. 06/694,308, Jan. 24, 1985, abandoned.

[30] Foreign Application Priority Data

| Jan. 28, 1984 | [DE] | Germany | 34 02 938 |
| Feb. 7, 1984 | [DE] | Germany | 34 07 025 |
| Feb. 15, 1984 | [DE] | Germany | 34 05 239 |
| Jun. 4, 1984 | [DE] | Germany | 34 20 738 |

[51] Int. Cl.$^6$ ................................................ A61K 31/62
[52] U.S. Cl. ........................................................ 514/161
[58] Field of Search ...................................... 514/458, 161

[56] References Cited

U.S. PATENT DOCUMENTS

| 3,149,037 | 9/1964 | Aiello et al. . | |
| 3,208,907 | 9/1965 | Delarue | 167/65 |
| 3,436,459 | 4/1969 | Klaui . | |
| 4,199,576 | 4/1980 | Reller | 424/230 |
| 4,241,054 | 12/1980 | Volpenhein et al. . | |
| 4,284,630 | 8/1981 | Yu et al. . | |
| 4,307,717 | 12/1981 | Hymes et al. . | |
| 4,386,072 | 5/1983 | Horrobin et al. . | |
| 4,412,986 | 11/1983 | Kawata et al. . | |
| 4,542,026 | 9/1985 | Rios . | |
| 4,627,850 | 12/1986 | Deters et al. . | |
| 4,684,524 | 8/1987 | Eckenoff et al. . | |
| 4,751,241 | 6/1988 | Motoyama et al. . | |
| 4,879,275 | 11/1989 | Minaskanian et al. . | |
| 4,938,960 | 7/1990 | Ismail | 424/195.1 |
| 5,153,001 | 10/1992 | Ismail . | |

OTHER PUBLICATIONS

Steiner, M., "Effect of Alpha–Tocopherol Administration on Platelet Function in Man", Division of Hematologic Research, The Memorial Hospital, Pawtucket, RI and Brown University, Providence, RI, pp. 73–77, (1983).

Cuzzocrea et al., "Veränderungen der Blutviskosität nach Vitamin E–gabe beim Kaninchen", Boll Soc Ital Biol Sper 59(5):679–85 (1983), pp. 1–7.

Williams et al., "Nephrotic Syndrome after the Application of Mercury Ointment", The Lancet, Original Articles, Sep. 1958, pp. 602–604.

Haeger, K., "Long–time Treatment of Intermittent Claudication with Vitamin E", The American Journal of Clinical Nutrition, Oct. 27, 1974, pp. 1179–1181.

Wilson et al., "Clinical Trial of Alpha–Tocopherol in the Prophylaxis of Thrombo–Embolism", The Lancet, Original Articles, Mar. 6, 1954, pp. 486–488.

Toone, W.M., "Effects of Vitamin E: Good and Bad", The New England Journal of Medicine, Nov. 1, 1973, pp. 979–980.

L.J. Machlin, "Vitamin E—A Comprehensive Treatise" (1990), pp. 578–583 and 586–595.

Sakharchuk et al., Chem.Abstract 101,48378(k) (1984).

Reynolds, E. F., "Martindale The Extra Pharmacopoeia", 28th edition, published 1982 by The Pharmaceutical Press (London) pp. 242 and 1663.

Chem. Abstract No. 98:221871, Nitto Electrical Industrial Co., Ltd., Japan, 1983.

Martindale, The Extra Pharmacopoeia, 28th ed. pp. 670–685, 1982.

*Primary Examiner*—Raymond Henley, III
*Attorney, Agent, or Firm*—Jacobson, Price, Holman & Stern, PLLC

[57] ABSTRACT

Vitamin E acts to enhance and improve the effect upon oral administration of coronary active vasodilators and/or blood circulation-promoters. The new use and new agents containing vitamin E are described.

1 Claim, No Drawings

AGENT FOR TREATING HEART DISEASES

This is a continuation of application Ser. No. 08/137,940, filed Oct. 19, 1993; which is a continuation of Ser. No. 07/913,885, filed Jul. 17, 1992, now abandoned; which is a continuation of Ser. No. 07/639,418, filed Jan. 10, 1991, now U.S. Pat. No. 5,153,001; which is a continuation of Ser. No. 07/290,848, filed Nov. 29, 1988 now abandoned; which is a continuation of Ser. No. 06/870,029, filed Jun. 3, 1986 now abandoned; which is a continuation of Ser. No. 06/694,308, filed Jan. 24, 1985 now abandoned.

BACKGROUND OF THE INVENTION

The present invention relates to a new use of vitamin E.

Vitamin E is known as an antioxidant and protective vitamin for phospholipids of the cell membrane. Vitamin E maintains the permeability and stability of the cell membrane; cf. Lucy, Annals N.Y. Academy of Science 203, 4 (1972). There has further been known that vitamin E has a membrane-sealing effect; cf. F. Mittelbach and G. Bodechtel, Munchner Medizinische Wochenschrift 110 (1968) 36: 1988–1993. In erythrocytes, the simplest cells of the human body, there has been found that vitamin E provides a protective effect for the cell membrane. In tests with animals and humans, it has been proven that anemia is a first signal of a deficiency of vitamin E. The hemolysis of the erythrocytes will normalize upon administration of high doses of vitamin E; cf. William J. Darbey Vitamin Horm., 26 (50) pp. 685–704 (1968) and Phelps DL Pediatrics 63 (6) pp. 933–935 (1979). From these literature references, it is apparent that after the oral administration of from 200 to 800 mg of vitamin E over a period of from 1 to 4 days, the hemolysis of the erythrocytes is significantly improved as compared to patients suffering from vitamin E deficiency.

Vitamin E has further been used to treat sickle cell anemia over a period of from 6 to 35 weeks; cf. Natt CL. Am. J. Clin. 33, pp. 968–971 (1980); Natt CL. Am. J. Clin. Nutr. 32, pp. 1359–1362 (1979); Gawlik G. M., Fed. Proc. 35 (3), p. 252 (1976) and Gorash L. Bieri J. G. et al., Univ. Conn. Farmington, Conn.

It has further been known that a daily dose of 750 mg of vitamin E over a period of from 3 to 6 months was successfully used to treat thalassemia patients, whereupon a normalization of the hemolysis of the erythrocytes was observed; cf. Kahane I. ISR. J. Med. 12 (1), pp. 11–15 (1976).

Vitamin E has further been successfully applied to patients suffering from an acute hepatitis or an alcoholic hepatitis having a deficiency in vitamin E in serum; cf. Yoshiakawa T., Takemura S., Kato H. et al., Japan. J. Gastrovent, 74/7, pp. 732–739 (1977). Eventually, vitamin E has been used to treat patients suffering from anemia due to an iron deficiency, in which treatment it caused an improvement or normalization of the lipid metabolism in the bone marrow to occur in the course of from 4 to 8 weeks; cf. Takoshi Itaga, Central Clinical Laboratory Nagasaki University of Medicine, Japan.

More detailed investigations of the resorption of vitamin E have resulted in the finding that a large portion of the vitamin E is destroyed by the gastric acid so that only part of the vitamin E can display its effects in the body; cf. Arthur Vogelsang in Angiology 21, pp. 275–79 (1970).

From Arzneimittel-Forschung 24, No. 2 (1974) 202 and 21, No. 3 (1971), there has been known that by means of vitamin E there results a substantial increase in tolerance of the heart-efficient glycosides, while a relation between the effect caused by vitamin E and the dose of vitamin E has been explicitly denied.

There has now been found that vitamin E surprisingly is suitable to enhance and improve the effects of coronary-active vasodilators and/or blood circulation promoters. These coronary-active agents, on the other hand, promote the activity of vitamin E.

This new range of indications was not foreseeable from the knowledge according to prior art and opens a new and wide field of applications of vitamin E.

The agents, whose activities can be improved according to the present invention, in the first place include the coronary-efficient nitro derivatives such as nitroglycerol (glycerol trinitrate), isosorbitol dinitrate, pentaerythritol tetranitrate and mononitrate compounds. These agents are used for the therapy and the prophylaxis of disturbances of coronary blood circulation and against coronary insufficiency and in the prophylaxis of angina pectoris.

It has been found that use of these active ingredients in combination with a sufficient dosage of vitamin E allows the duration of treatment to be substantially shortened. The symptoms of the diseases will be more rapidly reduced, so that after some time the applied dose of the nitro compound can be significantly lowered.

These results were not foreseeable and enable a therapy to be applied in which part of the chemically active compound is substituted by a substance of natural origin which, moreover, is present in every cell of the body.

Further agents whose effects can be enhanced according to the invention are agents promoting blood circulation such as Extract. Hippocastani and $\beta$-hydroxyethylrutoside, on the one hand, and nicotinic acid and nicotinic acid ester or derivatives thereof, respectively, such as xanthinol nicotinate and inositol nicotinate, dihydroergotoxine methanesulfonate, dihydroergocristine methanesulfonate, and dihydroergocornine methanesulfonate, on the other hand. It has been found that upon application of said agents in combination with a sufficient dose of vitamin E, the symptoms in many patients will be faster reduced and after some months the amounts of the vasodilators and/or blood circulation promoters can be lowered.

Crucial for the efficacy of vitamin E to enhance and improve the effects of coronary-efficient and/or blood circulation-promoting agents, above all, is a sufficient dosage which should be at least 80 mg. Lower dosages of vitamin E are useless, since large parts are destroyed by the gastric acid and thereby lose their activity; cf. Arthur Vogelsang, in: Angiology 21, pp. 275–279 (1970).

SUMMARY OF THE INVENTION

It is an object of the present invention to provide the use of vitamin E to enhance and improve the coronary-effective vasodilators and/or blood circulation-promoting agents. Therein the dosage should be in the range of from 80 to 500 mg, and preferably in the range of from 150 to 400 mg. Typical combination preparations contain from 200 to 400 mg of vitamin E.

It is another object of the present invention to provide agents to effect enhancement and improvement of the coronary-effective vasodilators and/or blood circulation-promoting agents characterized in that they contain vitamin E in a dose of from 80 to 500 mg, and preferably in a dose within the aforementioned ranges.

As the vitamin E, there may be employed natural vitamin E in the form of D-alpha-tocopherol and concentrates thereof and the respective acetates as well as synthetic D,L-alpha-tocopherol or its acetate.

The agents according to the invention contain conventional carriers and excipients in addition to the active ingredients and to the vitamin E. Since vitamin E is liquid at ordinary temperatures, drops and soft gelatin capsules particularly offer themselves as suitable application forms. The other active ingredients are incorporated in the vitamin E and, if desired, in a low-viscosity neutral oil and a solutizer such as Tween in a per se known manner. In this step, more specifically, there may be used the standard recipes of the firm Scherer, Eberbach, West Germany.

Suitable as further carriers and excipients are lactose, polyethyleneglycol, silica and its derivatives, and emulsifiers.

The simultaneous intake of vitamin E and heart glycosides ensures the regular intake of both active ingredients. Besides, the amount of heart glycosides can be reduced during the permanent application of the vitamin E capsule combination, and thereby a digitalis intoxication or side-effects caused by the digitalis can be avoided.

When heart glycosides, such as digoxine, acetyldigoxine etc. are being administered, attention must be paid to that the oxygen consumption in the heart is normal. In the case of an oxygen deficiency in the heart, the daily dose must be lowered. The oxygen consumption is economized or regulated, respectively, by the combination comprising vitamin E, so that a constant intake of heart glycoside becomes possible, i.e. the compatibility of the heart glycosides is increased. More specifically, due to the combination of the heart glycosides with vitamin E, a constantly lower dosage thereof can be applied over an extended period of time. In addition, vitamin E causes pain in the heart region to be reduced or eliminated.

There is also a possibility of alternating the intakes of a high dosage of heart glycosides in the absence of vitamin E with the combination comprising vitamin E and a lower digitalis dose according to the invention. Intake of the combination comprising vitamin E and heart glycoside(s) in one capsule will shorten the duration of the treatment and reduces the probability of a relapse and/or intoxication, respectively. Vitamin E also strengthens the heart muscle.

Vitamin E may be employed in any of its alpha-forms, in the free forms as well as in the forms of the esters. Vitamin E may be contained in an amount between 200 and 800 mg, and preferably between 300 and 600 mg, in each capsule.

The ester to be used may be the acetate, succinate, nicotinate or any other suitable ester. As the heart glycoside (s) there may be used, e.g., digoxine, digitoxine, acetyl-digoxine and strophantine, derivatives thereof or analogous mixtures, respectively.

As the neutral oil to be employed in the preparation of the capsules there may be used soybean oil or hydrogenated soybean oil, respectively, peanut oil, olive oil, triglycerides etc.

Further additives such as vitamin A or one or more vitamins of the B series, respectively, may be added. The capsule may also be resistent to gastric juice.

There has further been unexpectedly found that vitamin E does not undergo any chemical reaction with heart glycosides, but that it is very well compatible. Thus, according to the invention neutral oil is used as a diluent in the preparation of the capsules.

It has further been determined that vitamin E is suprisingly well transdermally resorbable and in the course thereof comes to cause particular effects in proximity of the site of resorption. Due to this finding vitamin E, more specifically, may be employed to treat heart diseases at a lower dosage with a higher efficacy.

Thus, under one more specific aspect, it is an object of the present invention to provide agents for treating heart diseases which agents are characterized in that they contain vitamin E and optionally other active ingredients in a transdermally resorbable form.

Such agents, for example, may be in the form of an ointment containing from 0.5 to 20% by weight of vitamin E in conventional carriers and excipients. Preferably, the vitamin E content is from 2 to 15% by weight.

Another possibility comprises incorporating vitamin E in a membrane plaster in an amount of from 0.05 to 5 g, wherefrom it may be transdermally resorbed. Such membrane plasters preferably contain from 0.5 to 3 g of vitamin E.

According to the invention, the vitamin E may be employed as D,L-alpha-tocopherol as well as a natural D-alpha-tocopherol.

As optionally further present active ingredients, there may more specifically be considered isosorbitol dinitrate and nitroglycerol (glycerol trinitrate), as these are also transdermally well resorbed. Further suitable are vasodilators and agents promoting blood circulation such as heparin sodium, Extract. Hippocastani, Extract. or *Tinct. arnicae,* β-hydroxyethylrutoside, salicylic acid ester, nicotinic-acid ester, more specifically the nicotinic acid benzylester.

The blood circulation in the heart may be enhanced by adding nifedipin. Such a combination is particularly suitable for a prophylactic treatment of patients endangered by a cardiac infarction.

Any conventional ointment bases are suitable for the formulations of the ointments, such as oil-in-water based on alcohol with polyethyleneglycols, but also *Eucerin cum aqua,* Ungentum Cordes or *Ungentum emulsificans.*

The present invention further describes the preferred use of embrocations such as, e.g., a cream, a gel, an ointment or a lotion containing vitamin E as a cardiac agent.

The ointment contains as a base 70 to 30% by weight, preferably 60 to 40% by weight, of water, 30 to 5% by weight, preferably 25 to 7% by weight, of Cetiol (oleyl oleate), and 30 to 2% by weight, preferably 25 to 2% by weight, of cetylstearylalcohol or other aliphatic alcohols.

In the place of the cetylstearylalcohol there may also be used altogether or in part other emulsifying alcohols, such as, e.g., aliphatic alcohols or wool wax alcohols or diols, respectively, stearinol, monoglycerides esterified with aliphatic acids or similar substances. There may also be added, e.g., paraffin or petrolatum or other suitable materials in order to render the ointment spreadable. Cetiol (oleyl oleate) may also be completely or partially replaced by other emulsifiers such as Tween 20 or Tween 80 etc.

It has been found that the best combination as a base for ointments or creams containing vitamin E is as follows:
30 to 20% by weight of cetylstearylalcohol,
20 to 10% by weight of Cetiol (oleyl oleate),
60 to 40% by weight of water (aqua conservata).
This ointment containing vitamin E will be immediately absorbed into the skin.

It has been known that ointment bases containing water such as *Unqentum emulsificans aguosum* and *Unquentum alkoholum lanae aquosum* are suitable for processing water-soluble active substances. However, it is surprising that ointment bases containing water to an amount of approximately more than 50% are very well suitable for processing lipophilic active substances such as vitamin E. Also the addition of a larger amount of emulsifier(s) such as Cetiol to, Unquentum Cordes or other ointment bases which do not contain water fail to cause the same properties as the above-mentioned ointment bases.

As the skin-stimulants or skin blood circulation-promoters there may be mentioned *Ol. juniperi, Ol. pini pumilionis* (dwarf pine oil), *Ol. eucalypti, Ol. rosmarinae, Tinct. camphorae* (or camphor, respectively), and as vasodilators there are to be mentioned, e.g., *Extract. calendulae* from the flower and *Herba calendulae*.

It has been determined that these vasodilators or blood circulation-promoters, respectively, significantly increase the effect of vitamin E and/or shorten the duration of the treatment, respectively, and remove the pain at long sight.

At long sight, the use of vitamin E provides a stabilization or permanent elimination of the symptoms, and, thus, the probability of a relapse to occur is very low.

The embrocations may also be prepared to be used in the liquid state, e.g. in alcohol as solutizer, such as in isopropyl alcohol or ethyl alcohol. For these embrocations vitamin E is used as the free alpha-tocopherol. Further derivatives of the blood circulation-promoters of vasodilators such as, e.g., trimethylolrutoside, may be employed.

For some time, membrane plasters have also been preferred to be employed for the application of transdermally resorbable active substances. A typical membrane plaster of the respective type has been described, for example, in the European Patent Application No. 80,300,038.9.

The new agents for the treatment of heart diseases are particularly suitable to effect a rapid alleviation and removal of pain. They result in a strengthening of the heart muscle and/or the coronary vessels, respectively. Thereby, upon a longer period of application, they also cause the resistance to burdening of the heart to be increased which may result even in an increase of the physical ability of the patient.

Thus, the agents according to the present invention are particularly well suitable for the therapy and the prophylaxis of coronary disturbances. They are further indicated for cases of coronary insufficiency and for the prophylaxis of angina pectoris.

The present invention is further illustrated by the following non-limiting examples showing typical combinations of active substances and dosages.

EXAMPLE 1

There are prepared capsules each containing
150 mg of xantinol nicotinate;
400 mg of vitamin E as D,L-alpha-tocopherol acetate or alphatocopherol concentrate; and
150 mg of soybean oil.

EXAMPLE 2

Capsules each containing
150 mg of β-hydroxyethyl rutoside;
300 mg of vitamin E; and
150 mg of soybean oil.

EXAMPLE 3

Capsules according to Example 2, but containing
100 mg of β-hydroxyethyl rutoside;
400 mg of vitamin E;
100 mg of soybean oil; and
20 mg of Tween 80.

EXAMPLE 4

Capsules each containing
120 mg of Extract. Hippocastani (20 mg of escin) or
200 mg of Extract. Hippocastani (35 mg of escin), respectively;
300 mg of vitamin E; and
130 mg of soybean oil.

EXAMPLE 5

Capsules each containing
250 mg of nicotinic acid;
400 mg of vitamin E; and
150 mg of soybean oil.

EXAMPLE 6

Capsules each containing
20, 40 or 60 mg of isosorbitol dinitrate on lactose as carrier;
400 mg of vitamin E (D-alpha-tocopherol acetate);
250 mg of nicotinic acid; and
200 mg of soybean oil.

EXAMPLE 7

Capsules each containing
5 mg of glycerol trinitrate on lactose as carrier;
400 mg of vitamin E (D-alpha-tocopherol acetate); and 200 mg of soybean oil.

EXAMPLE 8

Capsules each containing 0.1 mg of β-acetyldigoxin;
400 mg of D,L-alpha-tocopherol acetate; and
40 mg of soybean oil.

EXAMPLE 9

Capsules each containing
0.2 mg of β-acetyldigoxin;
400 mg of D,L-alpha-tocopherol acetate; and
40 mg of soybean oil.

EXAMPLE 10

Capsules each containing
0.25 mg of digoxin;
500 mg of D-alpha-tocopherol acetate;
100 mg of soybean oil; and
10,000 I.U. of vitamin A palpitate.

EXAMPLE 11

Capsules each containing
0.05 mg of digoxin;
400 mg of D,L-alpha-tocopherol acetate;
13.75 mg (25,000 I.U.) of vitamin A palmitate;
12.40 mg of peanut oil; and
50 mg of soybean oil.

EXAMPLE 12

Capsules each containing
0.07 mg of digoxin;
350 mg of D,L-alpha-tocopherol acetate; and
50mg of soybean oil.

EXAMPLE 13

A heart ointment containing vitamin E was prepared as follows: Eucerin cum aqua is stirred with D-alphatocopherol or D,L-alpha-tocopherol to give an ointment, so that 7.5 g of vitamin E are contained per 100 g of ointment.

EXAMPLE 14

In the same manner as described in Example 13, an ointment containing 7.5 g of D-alpha-tocopherol and 1.0 g of isosorbitol dinitrate per 100 g of ointment is obtained.

EXAMPLE 15

In the same manner as described in Example 13, an ointment containing 8.5 g of D-alpha-tocopherol per 100 g of ointment is obtained.

EXAMPLE 16

In the same manner as described in Example 13, an ointment containing 7 g of D-alpha-tocopherol and 10.000 I.U. of heparin sodium per 100 g of ointment is obtained.

EXAMPLE 17

In the same manner as described in Example 13, an ointment containing 9.5 g of D-alpha-tocopherol and 2 g Extract. Hippocastani standardized to at least 8% of escin per 100 g of ointment is obtained.

EXAMPLE 18

Capsules each containing
0.1 mg of β-acetyldigoxin;
400 mg of D,L-alpha-tocopherol acetate;
25,000 I.U. of vitamin A palmitate; and
40 mg of soybean oil.

EXAMPLE 19

Capsules each containing
0.2 mg of β-acetyldigoxin;
400 mg of D,L-alpha-tocopherol acetate;
25,000 I.U. of vitamin A palmitate; and
40 mg of soybean oil.

EXAMPLE 20

Capsules each containing
0.25 mg of digoxin;
500 mg of D-alpha-tocopherol acetate;
50,000 I.U. of vitamin A palmitate; and
100 mg of soybean oil.

EXAMPLE 21

Capsules each containing
10 mg of nifedipin;
400 mg of D,L-alpha-tocopherol acetate;
8,000 I.U. of vitamin A palmitate; and
200 mg of soybean oil.

EXAMPLE 22

Capsules each containing
10 mg of nifedipin;
400 mg of D-alpha-tocopherol acetate;
8,000 I.U. of vitamin A palmitate; and
200 mg of soybean oil.

EXAMPLE 23

Capsules each containing
20.0 mg of nifedipin;
500 mg of D-alpha-tocopherol acetate;
1,000 I.U. of vitamin A acetate; and
220 mg of soybean oil.

EXAMPLE 24

Capsules each containing
20.0 mg of nifedipin;
500 mg of D-alpha-tocopherol acetate; and
220 mg of soybean oil.

EXAMPLE 25

Capsules each containing
20.0 mg of nifedipin;
500 mg of D-alpha-tocopherol acetate;
6 mg of β-carotene; and
220 mg of soybean oil.

EXAMPLE 26

Ointment containing
10 g of D-alpha-tocopherol;
50,000 I.U. of heparin sodium; and
100 g of ointment base comprising
22 parts of cetylstearylalcohol,
18 parts of Cetiol and
60 parts of water (aqua conservata).

EXAMPLE 27

Ointment containing
7 g of vitamin E (D-alpha-tocopherol);
1 g of nicotinic acid benzyl ester;
1 g of camphor; and
100 g of ointment base comprising
17 parts of cetylstearylalpohol,
8 parts of white petrolatum,
15 parts of cetiol
60 parts of water (aqua conservata).

EXAMPLE 28

Ointment containing
7 g of vitamin E and
15 g of *Tinct. calendulae;* and
100 g of ointment base comprising
13 parts of wool wax alcohol;
2 parts of cetylstearylalcohol;
20 parts of Cetiol;
5 parts of paraffin;
50 parts of water (aqua conservata).

EXAMPLE 29

Ointment containing
8 g of vitamin E (D,L-alpha-tocopherol);
1.5 g of rosemary oil;
1 g of Extract. Hippocastani (standardized to at least 8% of escin);
1 g of juniper oil; and
100 g of ointment base according to Example 26.

EXAMPLE 30

Solution comprising
5 g of vitamin E (D-alpha-tocopherol);
1 g of dwarf pine oil (*Ol. pini pumilionis*);
1 g of eucalyptus oil;
1 g of juniper oil; and
100 g of isopropyl alcohol;

EXAMPLE 31

Ointment containing
7 g of D,L-alpha-tocopherol concentrate;
2 g of *Tinct. arnicae;*
2 g of salicylic acid β-hydroxyethylester; and
100 g of ointment base according to Example 26.

EXAMPLE 32

Solution comprising
7.0 g of vitamin E;
1.0 g of dwarf pine oil;
1.0 g of *Tinct. arnicae;* and
100 g of isopropyl alcohol.

EXAMPLE 33

Ointment containing
9.0 g of vitamin E and
20.0 g of *Tinct. calendulae* and
100 g of ointment base according to Example 26.

What is claimed is:

1. A method of treating or for prophylaxis of a disease selected from the group consisting of ischemic heart diseases, coronary circulatory disorders, and cardiac insufficiency comprising orally administering to a mammal in need thereof a composition comprising 80 to 800 mg vitamin E, an effective amount of salicylic acid ester, and a pharmaceutically acceptable carrier or adjuvant.

* * * * *